United States Patent [19]

Mazoyer

[11] 4,271,191

[45] Jun. 2, 1981

[54] METHOD OF TREATING HYPERURICEMIA AND GOUT

[75] Inventor: France Mazoyer, Castres, France

[73] Assignee: Pierre Fabre S.A., Paris, France

[21] Appl. No.: 105,420

[22] Filed: Dec. 19, 1979

[51] Int. Cl.³ .................. A61K 31/19; A61K 31/505; A61K 31/165

[52] U.S. Cl. .................... 424/317; 424/251; 424/324

[58] Field of Search ........................ 424/317, 251, 324

[56] References Cited

U.S. PATENT DOCUMENTS

| | | | |
|---|---|---|---|
| 4,008,323 | 2/1977 | Cousse et al. | 424/248.54 |
| 4,058,558 | 11/1977 | Cousse et al. | 424/250 |

OTHER PUBLICATIONS

Merck Index, 9th Ed., 1976, pp. 39, 318.
Merck Manual, 12th Ed., 1972, pp. 1101–1107.

*Primary Examiner*—Frank Cacciapaglia, Jr.
*Attorney, Agent, or Firm*—Gordon W. Hueschen

[57] ABSTRACT

The present application relates to the treatment of hyperuricemias, including the prevention and treatment of gout, using the compound Itanoxone or a pharmaceutically-acceptable salt thereof. The compound Itanoxone has the chemical name 2′-chloro-4,4-biphenyl-4-oxo-2-methylene-butyric acid, and may alternatively be named 2-methylene 4-oxo 4-(4′-ortho-chlorophenylphenyl)-butyric acid. The formula for the compound is as follows:

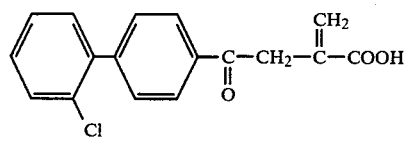

The international common name of this compound is "Itanoxone". Pharmaceutical compositions of the active ingredient, suitable for carrying out the method of the invention, and combinations thereof with other active ingredients, particularly colchicine and allopurinal, are also disclosed.

7 Claims, No Drawings

METHOD OF TREATING HYPERURICEMIA AND GOUT

BACKGROUND OF THE INVENTION

1. Field of Invention

Treatment of hyperuricemias, treatment and prevention of gout.

2. Prior Art

Numerous drugs have, in the past, been proposed for the treatment of hyperuricemias and the prevention and treatment of gout. Methods of treating subjects afflicted with hyperuricemias and gout, and efforts to prevent attacks of gout in subjects having a tendency toward hyperuricemias and otherwise, have left much to be desired. It is apparent that additional methods for the treatment of hyperuricemias and for the prevention and treatment of gout would be highly desirable. The present invention provides such an additional and highly advantages method of treatment and prevention.

SUMMARY OF THE INVENTION

The present invention relates to a method for the treatment of hyperuricemias and for the treatment or prevention of gout by the administration to a patient or subject in need thereof a hypouricemic amount of Itanoxone or a pharmaceutically-acceptable salt thereof.

The compound Itanoxone has the chemical name 2′-chloro-4,4-biphenyl-4-oxo-2-methylene-butyric acid, and may alternatively be named 2-methylene 4-oxo 4-(4′-ortho-chlorophenylphenyl)-butyric acid. The formula for the compound is as follows:

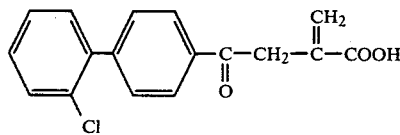

The international common name of this compound is "Itanoxone".

In the text hereof this compound will be referred to as Itanoxone and sometimes by its code name: F 1379. This product is furthermore the subject matter of U.S. Pat. No. 4,058,558, issued Nov. 15, 1977 to H. COUSSE, G. MOUZIN, and J. P. RIEU and U.S. Pat. No. 4,008,323, issued Feb. 15, 1977 to H. COUSSE, G. MOUZIN, J. P. RIEU and A. DELHON, wherein the compound is generally referred to by its code name F 1379.

In accordance with the present invention, the compound has demonstrated an unexpected but valuable hypouricemizing action in clinical experiments on man. This unexpected activity, which is not found in animal pharmacology, was discovered during the course of analyzing the biological parameters of patients treated within the scope of the indications pursuant to the above-mentioned patents, namely, as analgesics, anti-inflammatories, and as hypocholesterolemics (cholesterol-reducing agents).

This new activity, which appears at doses of about 125 to about 500 mg/day, represents an interesting and valuable new potential for the use of this product in the treatment of hyperuricemia, and especially in the treatment and prevention of gout and its most uncomfortable and undesirable symptoms.

PHARMACOLOGY

The first studies carried out with F 1379 have shown hypouricemizing effects which manifest themselves both in normal uricemic patients and in patients who are very slightly uricemic, i.e., in incipient uricemias. In the course of these studies, the product was administered orally.

This action takes placed by a predominant uricosuric mechanism. This has been established by studies on healthy volunteers, as hereinafter reported.

The study was carried out in an open test.

The patients:

The patients comprised seven (7) men and one (1) woman.

Average age: 32±5 years.

Average weight: 63.15±2.61 kg

Their renal function was normal; creatinine clearance 80 ml/min/1.73 $m^2$.

The test result:

The F 1379 was administered for four (4) consecutive days in a dosage amount of 500 mg/day in the morning (namely, as 2–250 mg tablets).

The course of the test:

Clinical and biological balance sheets were drawn up:

on day 0 of the test during the administration of the F 1379 (days 1, 2, 3, 4)

on the day following the discontinuation of the F 1379 (day 5).

The statistical exploitation:

The parameters studied on each day of the test are evaluated by their mean value and the standard difference $$\left( \frac{m + S}{\sqrt{n}} \right).$$

Comparisons were carried out on days 1, 2, 3, 4 and 5 of the test, as compared with day 0, by the student t test for paired series of low effective $$t = \frac{m}{s/\sqrt{n}}$$

(in which m and S designate the mean and the standard difference, estimated on the sample of n differences).

Results:

The results are set forth in the accompanying Table I.

F 1379 produces a hypouricemic action by means of a uricosuric mechanism.

As a matter fact, there is to be noted:

an increase in the uraturia and in the uric-acid clearance and the ratio of uric acid clearance to creatinine clearance.

no change in the oxypurine and purine content of the blood and urine.

no variation in the creatinine clearance.

Furthermore, F 1379 does not cause any changes in the urinary excretion of sodium, potassium, calcium, lysozyme, or $\beta$-2-microglobulin.

CLINICAL STUDIES

F 1379 has been successfully employed in the treatment of essential gout and non-gout hyperuricemias and in secondary hyperuricemias of iatrogenic origin (thiazinic).

In the treatment of the gout patient, the product has been successfully administered:

in attack treatment: in a dose of 375 mg/day for one month.

in maintenance treatment: 125 to 250 mg/day.

Beginning after the first month of treatment, the uricemia is normalized. It remains at amounts of less than 300 μmol/liter throughout the period of administration of the product.

Furthermore, no attack of gout was found:

upon the discontinuance of the administration of colchicine, or in patients who noted a reduction of appetite accompanied by loss in weight.

Finally, the product is tolerated well, both clinically and biologically.

No effect is noted with respect to the blood parameters (glycemia, urea, sodium, potassium, total proteins, leukocyte count, red cell count, erythrocyte count, and total blood count) with the exception of the total cholesterol content, which drops 21% ($p<0.01$) in four (4) days, as is to be expected.

The triglycerides are not modified.

In conclusion, in accordance with the present invention, F 1379 (Itanoxone) can be used successfully in the oral treatment of hyperuricemia. In attack treatment, and preferably but not necessarily in association with colchicine or allopurinol, the dose will be two (2) to three (3) tablets of 125 mg/day; after two (2) weeks, or when the uricemia has been normalized, it will be necessary to continue with maintenance treatment by administering one (1) tablet of 125 mg every day or every two days.

This treatment can obviously be modified considerably. The above indications merely illustrate the invention without limiting its scope.

The following Examples of specific pharmaceutical forms are likewise given by way of illustration only and are not to be construed as limiting.

SPECIFIC PHARMACEUTICAL FORMS

The palliative, ameliorative, or preventive treatment in accord with the present invention can be carried out by utilizing various pharmaceutical forms.

By way of illustration and not of limitation, we cite a few representative pharmaceutical forms which are useful in the practice of the method of the invention.

(1) Tablets of 125 mg employing, as representative excipient, lactose, stearic acid, gelatin, or the like.

(2) Gelatin capsules of 125 mg (3) Scored tablets of 250 mg employing, as excipient, silica, magnesium stearate, starch, or the like.

(4) Drops of neutral pH—either aqueous or alcoholic—five (5) grams of Itanoxone per 100 ml, preferably in the form of a therapeutically-acceptable salt, e.g., the piperazine or dimethylaminoethanol salt.

(5) In all of the foregoing forms, the Itanoxone can also be associated with colchicine or allopurinol in exactly the same pharmaceutical specialty as described, said combination also being directed at and useful in the treatment of hyperuricemia.

Although other modes of application may be employed, the oral route is obviously preferred for reasons of convenience.

Innumerable pharmaceutically-acceptable salts of Itanoxone are readily available and conventionally prepared, such as the sodium, potassium, lithium, arginine, piperazine, dimethylaminoethanol, or like salts. Salts with alkali and alkaline-earth metals, amino acids such as arginine and lysine, or amines such as diloweralkylaminoalkanols and the like are preferred, as are salts with piperazine and the like. Thus, the active ingredient is the free Itanoxone acid or a pharmaceutically-acceptable salt thereof. Numerous pharmaceutically-acceptable salts are disclosed in the aforesaid U.S. Pat. Nos. 4,008,323 and 4,058,558, which also discloses the compound Itanoxone under the code name F 1379.

From the foregoing, it is apparent that the compounds, namely, Itanoxone and its pharmaceutically-acceptable salts, are active hypouricemic compounds, which may be used in the treatment of hyperuricemias and particularly in the treatment and prevention of gout. As such, these compounds may be utilized either per se or preferably in the form of pharmaceutical compositions together with usual pharmaceutical diluents, carriers, or adjuvants, according to the customary procedure of the art. They may, in this manner, be embodied into pharmaceutical compositions, comprising an effective hypouricemic amount of the active ingredient together with a pharmaceutically-acceptable carrier. They may be administered in the form of such pharmaceutical compositions wherein the amount of active ingredient is advantageously 100 mg, 250 mg, or greater or lesser amounts, depending upon the patient involved and the exact syndrome being treated, depending of course upon the judgement of the physician in charge, body weight of the patient, et cetera. The daily regimen is 125 to 500 mg per day, in attack treatments a dosage of approximately 375 mg per day for a period of one month being a satisfactory dosage regimen and, in maintenance treatment, a dosage of 125 to 250 mg per day being adequate. The daily regimen is accordingly any number, e.g., one to four, such unit dosages as previously mentioned, for attack treatment or maintenance dosage for ameliorative or prophylactic treatment of the exact condition involved. Therefore, in the treatment of hyperuricemia, the active ingredient is administered to a subject suffering from hyperuricemia in an effective hypouricemic amount. Thus, the active ingredients have been successfully employed in the treatment of essential gout, non-gout hyperuricemia, and in secondary hyperuricemias of iatrogenic origin of a thiazinic nature. When the compounds or compositions are employed for their hyperuricemic effect, they are administered to a subject in need thereof, particularly a subject suffering from hyperuricemia or gout, in an effective hypouricemic amount. For all uses, the compounds or compositions are preferably administered orally, and preferably are administered in the form of the free acid or a pharmaceutically-acceptable salt thereof. All of the usual diluents, carriers, or adjuvants may be employed to facilitate administration of the compounds of the invention. They may obviously be administered in combination with other active ingredients in accord with standard practice in the art, particularly with colchicine or allopurinol, either concurrently or in the same dosage form in combination with the additional active ingredient. Particularly acceptable dosage forms are tablets, gelatine capsules, scored tablets, or aqueous or alcoholic drops having a neutral pH, in which case aqueous drops are preferred and the Itanoxone is advantageously in the form of a therapeutically-acceptable salt thereof to facilitate solubility in the medium employed.

It is to be understood that the invention is not to be limited to the exact details of operation or exact compounds, compositions, methods, or procedures shown and described, as obvious modifications and equivalents will be apparent to one skilled in the art.

TABLE I

| Parameters | J0 | J + 1 | J + 2 | J + 3 | J + 4 | J + 5 |
|---|---|---|---|---|---|---|
| Urine volume (ml/24 hours) | 1410.62 ± 161.19 | 1425 ± 110.41 NS (ddl 7 t = 0.09) | 1423.75 ± 148.07 NS (ddl 7 t = 0.11) | 1496.25 ± 89.46 NS (ddl 7 t = 0.59) | 1667.5 ± 113.55 NS (ddl 7 t = 1.91) | 1655 ± 131.22 +17% $p<0.05$ (ddl 7 t = 2.58) |
| Creatininemia ($\mu$ mol/liter) | 91.25 ± 4.41 | 88.75 ± 7.20 NS (ddl 7 t = 0.57) | 85 ± 5.68 $p<0.05$ (ddl 7 t = 2.37) | 82.50 ± 5.60 $p<0.05$ (ddl 7 t = 2.96) | 85 ± 6.28 NS (ddl 7 t = 1.66) | 90 ± 8.04 NS (ddl 7 t = 0.22) |
| Creatininuria ($\mu$ mol/liter) | 10162 ± 1748 | 9837 ± 1441 NS (ddl 7 t = 0.31) | 10112 ± 1842 NS (ddl 7 t = 0.05) | 9475 ± 1346 NS (ddl 7 t = 0.64) | 8275 ± 1143 NS (ddl 7 t = 1.26) | 9300 ± 1381 NS (ddl 7 t = 0.61) |
| Creatinine clearance (ml/min) | 96 ± 4.33 | 105 ± 10.61 NS (ddl 7 t = 0.97) | 103.87 ± 7.15 NS (ddl 7 t = 1.60) | 115.37 ± 11.10 NS (ddl 7 t = 1.86) | 109.12 ± 10.30 NS (ddl 7 t = 1.53) | 115.12 ± 34.68 NS (ddl 7 t = 1.75) |
| Uricemia ($\mu$ mol/liter) | 300 ± 21.94 | 285 ± 21.02 −5% NS (ddl 7 t = 1.77) | 255 ± 24.85 −15% $p<0.01$ (ddl 7 t = 3.54) | 268.75 ± 22.38 −10% NS (ddl 7 t = 1.47) | 242.50 ± 19.02 −19% $p<0.01$ (ddl 7 t = 3.56) | 256.25 ± 24.31 −15% NS (ddl 7 t = 1.62) |
| Uraturia ($\mu$ mol/liter) | 2375 ± 121.36 | 2700 ± 204.14 +14% NS (ddl 7 t = 1.84) | 2975 ± 218.89 +26% $p<0.01$ (ddl 7 t = 3.85) | 2875 ± 158.30 +22% $p<0.02$ (ddl 7 t = 3.21) | 2737.50 ± 215 +16% $p = 0.05$ (ddl 7 t = 2.37) | 2725 ± 257.63 +15% NS (ddl 7 t = 1.73) |
| Uraturia ($\mu$ mol/24 hours) | 3245 ± 276 | 3794 ± 311 +17% $p<0.05$ (ddl 8 t = 2.56) | 4085 ± 338 +26% $p<0.05$ (ddl 8 t = 2.53) | 4226 ± 169 +30% $p<0.01$ (ddl 8 t = 3.94) | 4438 ± 209 +37% $p<0.01$ (ddl 8 t = 5.13) | 4349 ± 293 +34% $p<0.01$ (ddl 8 t = 4.29) |
| Uric acid clearance (ml/min) | 8.01 ± 1.12 | 9.65 ± 1.18 +20% $p<0.01$ (ddl 7 t = 3.85) | 11.69 ± 1.23 +46% $p<0.01$ (ddl 7 t = 4.65) | 11.37 ± 0.92 +42% $p<0.02$ (ddl 7 t = 3.07) | 13.15 ± 1.04 +63% $p<0.01$ (ddl 7 t = 5.37) | 13.24 ± 1.78 +65% $p<0.02$ (ddl 7 t = 5.23) |
| Uric acid clearance/ creatinine clearance | 0.07 ± 0.008 | 0.09 ± 0.01 NS (ddl 7 t = 1.51) | 0.11 ± 0.01 $p<0.01$ (ddl 7 t = 3.86) | 0.09 ± 0.009 NS (ddl 7 t = 1.64) | 0.11 ± 0.006 $p<0.02$ (ddl 7 t = 3.41) | 0.11 ± 0.009 $p<0.02$ (ddl 7 t = 3.05) |
| Plasma oxypurines and purines ($\mu$ mol/liter) | 14.06 ± 2.95 | | | | | 12.56 ± 2.03 NS (ddl 7 t = 0.47) |
| Urinary oxypurines plus purines ($\mu$ mol/24 hours) | 255.29 ± 30.88 | 279.80 ± 38.93 NS (ddl 7 t = 1.97) | 280.84 ± 37.90 NS (ddl 7 t = 0.44) | 270.95 ± 35.48 NS (ddl 6 t = 0.53) | 270.48 ± 37.44 NS (ddl 7 t = 0.51) | 309.26 ± 45.15 NS (ddl 7 t = 1.44) |

I claim:

1. A method for the treatment of hyperuricemia which comprises orally administering to a hyperuricemic subject in need thereof an effective hypouricemic amount of a compound selected from the group consisting of 2-methylene 4-oxo 4-(4′-ortho-chlorophenylphenyl)-butyric acid and a therapeutically-acceptable salt thereof.

2. The method of claim 1 wherein the method is carried out for the treatment or prevention of gout.

3. The method of claim 1 wherein the active hypouricemic compound is administered in a daily dose of 125 to 500 mg per day.

4. The method of claim 1 wherein the active compound is orally administered in the form of a pharmaceutical composition thereof together with a pharmaceutically-acceptable carrier.

5. The method of claim 1 wherein the active compound is administered orally in the form of a pharmaceutical composition thereof together with a pharmaceutically-acceptable carrier, wherein the amount of active ingredient is between about 125 and 500 mg per day, administered in a dosage unit form containing between about 100 and 250 mg per dosage unit.

6. The method of claim 4 wherein the active ingredient is 2-methylene 4-oxo 4-(4′-ortho-chlorophenylphenyl)-butyric acid itself as the free acid.

7. The method of claim 1 wherein the active hypouricemic compound is administered in a daily dose of 125 to 250 mg per day.

* * * * *

UNITED STATES PATENT AND TRADEMARK OFFICE
CERTIFICATE OF CORRECTION

PATENT NO. : 4,271,191

DATED : June 2, 1981

INVENTOR(S) : France Mazoyer

It is certified that error appears in the above—identified patent and that said Letters Patent is hereby corrected as shown below:

[57] ABSTRACT, last two (2) lines; "allopurinal," should read
-- allopurinol, --
Col. 1, line 21; "advantages" should read -- advantageous --
Cols. 5 & 6, Table 1, under column heading "J + 2", line 16; "218.89" should read -- 218.39 --

Signed and Sealed this

Sixth Day of October 1981

|SEAL|

Attest:

GERALD J. MOSSINGHOFF

Attesting Officer     Commissioner of Patents and Trademarks